United States Patent
Bartlett et al.

(10) Patent No.: US 9,222,876 B2
(45) Date of Patent: Dec. 29, 2015

(54) LIGHT SCATTERING FLOW CELL DEVICE

(75) Inventors: Jonathan Todd Bartlett, Duxbury, MA (US); Thomas Lloyd Remsen, Weymouth, MA (US); Trevor Julian Havard, Whitinsville, MA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 784 days.

(21) Appl. No.: 13/121,148

(22) PCT Filed: Sep. 23, 2009
(Under 37 CFR 1.47)

(86) PCT No.: PCT/US2009/058104
§ 371 (c)(1),
(2), (4) Date: Jul. 22, 2011

(87) PCT Pub. No.: WO2010/036736
PCT Pub. Date: Apr. 1, 2010

(65) Prior Publication Data
US 2012/0250023 A1     Oct. 4, 2012

Related U.S. Application Data

(60) Provisional application No. 61/100,044, filed on Sep. 25, 2008.

(51) Int. Cl.
*G01N 21/00* (2006.01)
*G01N 21/01* (2006.01)
*G01N 33/36* (2006.01)
(Continued)

(52) U.S. Cl.
CPC ............ *G01N 21/05* (2013.01); *G01N 21/53* (2013.01); *G01N 2021/4716* (2013.01); *G01N 2021/513* (2013.01)

(58) Field of Classification Search
CPC ............... G01N 21/05; G01N 21/53; G01N 2021/4716; G01N 2021/513; G01N 2021/53
USPC ......... 356/338, 244–246, 440, 337, 432, 436, 356/439, 342, 343
See application file for complete search history.

(56) References Cited

U.S. PATENT DOCUMENTS 4,575,424 A * 3/1986 Allington et al. .......... 210/198.2
5,734,468 A   3/1998 McNeal
(Continued)

FOREIGN PATENT DOCUMENTS

DE     3813718 A1   11/1989
EP     0182618 A2    5/1986
(Continued)

OTHER PUBLICATIONS

EPO Office Action dated Jul. 18, 2014 for EPO Application No. 09816812.3-1553.

*Primary Examiner* — Tarifur Chowdhury
*Assistant Examiner* — Sunghee Y Gray (57) ABSTRACT

A flow cell device includes a body having a hollow bore in which a liquid sample may reside. An electromagnetic beam may be directed through the body and into the bore to irradiate the liquid sample. The beam may be directed orthogonal to an axis of the bore. A light ray produced as a result of the irradiation may likewise be directed orthogonal to the bore axis along the same plane as the beam, and received by a detector. The body may be secured between a liquid inlet structure and a liquid outlet structure.

20 Claims, 8 Drawing Sheets

(51) Int. Cl.
  *G01J 1/04* (2006.01)
  *G01N 21/05* (2006.01)
  *G01N 21/53* (2006.01)
  *G01N 21/47* (2006.01)
  *G01N 21/51* (2006.01)

(56) References Cited

U.S. PATENT DOCUMENTS

| | | | |
|---|---|---|---|
| 5,737,078 | A | 4/1998 | Takarada et al. |
| 6,784,981 | B1 | 8/2004 | Roche et al. |
| 6,813,303 | B2 | 11/2004 | Matsuda et al. |
| 2003/0086087 | A1 | 5/2003 | Quist et al. |
| 2004/0004717 | A1* | 1/2004 | Reed ............................ 356/338 |
| 2007/0064226 | A1* | 3/2007 | Kolp et al. .................... 356/246 |
| 2007/0211244 | A1* | 9/2007 | Hilmer et al. ................. 356/246 |

FOREIGN PATENT DOCUMENTS

| | | |
|---|---|---|
| EP | 1225439 A2 | 7/2002 |
| EP | 1515131 A1 | 3/2005 |
| EP | 1884762 A2 | 2/2008 |
| WO | 98/52013 A1 | 11/1998 |
| WO | 2004106916 A1 | 12/2004 |
| WO | 2010/036736 A2 | 4/2010 |

\* cited by examiner

LIGHT SCATTERING FLOW CELL DEVICE

FIELD OF THE INVENTION

The present invention relates generally to flow cells utilized for handling liquid samples to be irradiated by a light source in the course of performing light scattering techniques, and to apparatus, systems and methods utilizing such flow cells.

BACKGROUND OF THE INVENTION

Light scattering techniques typically utilize a flow cell constructed from an optically transmitting material such as glass. The flow cell is configured to enable passage of a liquid sample through a bore formed in the solid material of the flow cell. A laser beam is directed through the solid material into the bore where it irradiates the liquid sample residing therein. In response to this irradiation, light rays propagate from the bore through the solid material at various angles. One or more light detectors situated external to the flow cell receive the light rays and typically convert the optical signal into an electrical or digital signal, which is thereafter processed and conditioned by electronics as needed to derive information regarding the analytes contained in the irradiated liquid sample.

Two commonly utilized light detectors are a static light detector and a dynamic light detector. The static light detector operates on the principle of light scattering intensity measurement (or static scattering, or Rayleigh scattering). The light intensity scattered by a molecule in solution that is small compared with the wavelength of the incident laser beam is proportional to the concentration multiplied by the molecular weight. Thus, for example, if the concentration of the molecules in solution is known or is measured during the analysis process, the molecular weight averages and distributions can be determined. The dynamic light detector operates on the principle of dynamic light scattering measurement (or quasi-elastic light scattering, or photon correlation spectroscopy). In dynamic light scattering detection, the translational diffusion coefficient of the molecules moving randomly in the solution is calculated from the autocorrelation function of the scattered light. These very small signal values may be collected by utilizing a solid state photon counter such as an avalanche photodiode and autocorrelator electronics incorporating high-speed digital signal processors. From the diffusion constant, the hydrodynamic radius can be calculated by utilizing the Stokes-Einstein equation.

An ongoing need exists for improvements in the design of flow cells utilized in light scattering processes. Such improvements include, for example, miniaturization so that the flow cell may be successfully utilized in a wide range of analytical systems such as various types of chromatography systems, as well as enhanced performance (e.g., signal-to-noise ratio, data resolution, instrument sensitivity, etc.). In addition, the flow cell and its corresponding components should be designed so as to be flexible and versatile to meet the needs of a wide variety of light scattering processes.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a flow cell device includes a solid, optically transmitting flow cell body, a liquid inlet structure and a liquid outlet structure. The flow cell body includes an outer surface and has a hollow bore. The hollow bore includes a liquid inlet end opening at the outer surface, and a liquid outlet end opening at the outer surface at a location axially opposite to the liquid inlet end. The liquid inlet structure includes a first protruding section contacting the liquid inlet end and extending to the hollow bore. The liquid inlet structure has a liquid inlet port formed in the first protruding section and fluidly communicating with the hollow bore. The liquid outlet structure includes a second protruding section contacting the liquid outlet end and extending into the hollow bore. The liquid outlet structure has a liquid outlet port formed in the second protruding section and fluidly communicating with the hollow bore.

According to another implementation, a flow cell device includes a solid, optically transmitting flow cell body, a laser source, and a light detector. The flow cell body has a central axis. The flow cell body includes a flat liquid inlet surface orthogonal to the central axis and having a circular perimeter, a flat liquid outlet surface parallel with the liquid inlet surface and having a circular perimeter, and a sidewall axially extending from the perimeter of the liquid inlet surface to the perimeter of the liquid outlet surface. The sidewall has a spherical outer profile. The flow cell body further has a hollow bore formed through the flow cell body along the central axis. The laser source is oriented relative to the flow cell body so as to direct a laser beam along a central plane of the flow cell body and through the hollow bore, the central plane being orthogonal to the central axis. The light detector is oriented relative to the flow cell body so as to receive a light ray propagating from the hollow bore and along the central plane.

According to another implementation, a flow cell device includes a solid, optically transmitting flow cell body, a mounting member, and one or more light detectors. The flow cell body includes a spherical outer surface. The flow cell body has a central axis, a hollow bore formed through the flow cell body along the central axis, and a central plane orthogonal to the central axis. The mounting member includes a curved surface facing the flow cell body and parallel with the spherical outer surface. The mounting member has a plurality of radial mounting bores opening at the curved surface. The radial mounting bores have respective mounting bore axes collinear with respective radii extending from the hollow bore along the central plane at different angles relative to the central axis.

According to another implementation, a method for making a light-scattering measurement of a liquid sample is provided. The liquid sample is introduced into a hollow bore of a solid, optically transmitting flow cell body, the hollow bore being oriented along a central axis. An electromagnetic beam is directed through the flow cell body and into the hollow bore along a central plane of the flow cell body orthogonal to the central axis, to irradiate the liquid sample and produce a light ray. The light ray is directed along the central plane away from the hollow bore. The light ray is received at a light detector positioned external to the flow cell body.

According to another method, a flow cell body is assembled between a liquid inlet structure and a liquid outlet structure, by contacting a first protruding section of the liquid inlet structure with a liquid inlet end of the hollow bore and contacting a second protruding section of the liquid outlet structure with a liquid outlet end of the hollow bore.

According to another method, a plurality of light detectors is mounted to a plurality of radial mounting bores of a mounting member. The mounting member includes a curved surface facing the flow cell body and parallel with a spherical outer surface portion of the flow cell body. The radial mounting bores open at the curved surface and have respective mounting bore axes collinear with respective radii extending from the hollow bore along the central plane at different angles relative to the central axis.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

Figures 1, 3:
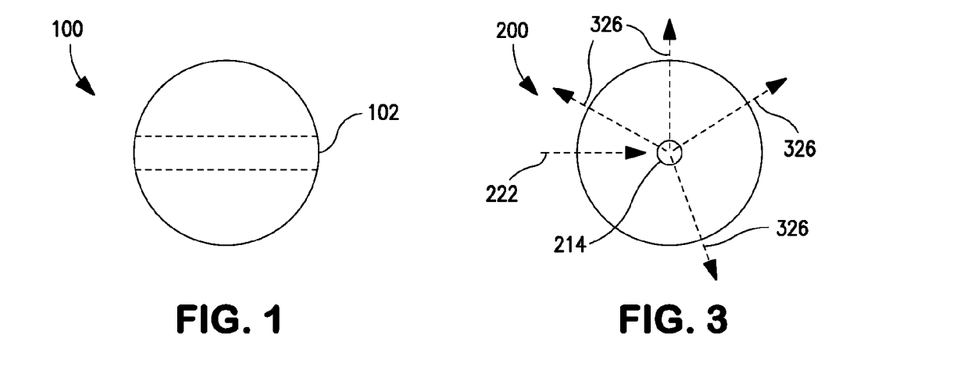
FIG. 1 is a view of a solid, polished glass sphere, which is provided to illustrate an example of how the flow cell of the present invention may be fabricated.
FIG. 3 is a top view of the flow cell illustrated in FIG. 2.

FIG. 1 is a view of a solid sphere 100, which is provided to illustrate an example of how the flow cell of the present invention may be fabricated. The sphere 100 may be constructed from any suitable optically transmitting material such as, for example, various glasses (e.g., fused silica). The outer surface of the sphere 100 may be polished or otherwise optimized for optical transmission. In the present example, the sphere 100 has a diameter of approximately 35 mm although in other examples the diameter may be greater or less than 35 mm. A central section 102 of the sphere 100, having a desired thickness about a given plane passing through the center of the sphere 100 (a horizontal plane in the present example), is machined out from the sphere 100 as indicated by two parallel dashed lines in FIG. 1.

Figure 2:
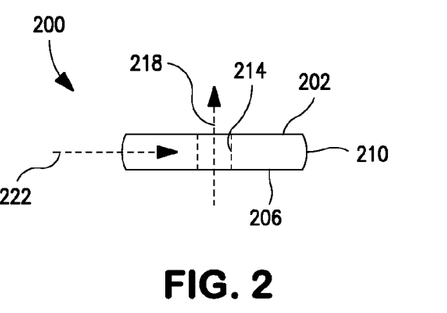
FIG. 2 is a view of an example of a flow cell according to an implementation of the present invention.

A flow cell 200 is formed as a result, as illustrated in FIG. 2. The flow cell 200 is generally shaped as a flat disc defined by a flat top surface for flat liquid outlet surface) 202 of circular area (thus having a circular perimeter), a flat bottom surface for flat liquid inlet surface) 206 of circular area (thus having a circular perimeter) parallel to the top surface 202, and a circular sidewall 210 between the top surface 202 and the bottom surface 206. The sidewall 210 retains the spherical outer profile of the sphere 100 from which the flow cell 200 is formed, and extends from the perimeter of the flat bottom surface (liquid inlet surface) 206 to the perimeter of the flat top surface (liquid outlet surface) 202. In the present example, the thickness of the flow cell 200 (in the present example, in the vertical direction from the top surface 202 to the bottom surface 206) is approximately 5 mm although in other examples may be greater or less than 5 mm. As also illustrated in FIG. 2, the center of the flow cell 200 is then drilled out to form a cylindrical, hollow central bore 214 of precise dimensions. In the present example, the central bore 214 has a diameter of approximately 3 mm although in other examples the diameter may be greater or less than 3 mm. The flat top surface (liquid outlet surface) 202 and flat bottom surface (liquid inlet surface) 206 are orthogonal to the central axis of the central bore 214. The central bore 214 has opposing axial ends that open at the respective top surface 202 and bottom surface 206. One end serves as a liquid inlet into the central bore 214 and the other end serves as a liquid outlet from the central bore 214.

In use, a liquid sample containing analytes of interest is flowed through the central bore 214 of the flow cell 200 as indicated by an arrow 218. With the flow cell 200 oriented as illustrated in FIG. 2, the direction of liquid flow 218 is vertical and upward, although the direction of liquid flow 218 may be different when the flow cell 200 is oriented differently. While the liquid sample resides in the central bore 214, a laser beam is directed along a direction orthogonal to the axis of the central bore 214, which in the present example is a horizontal direction as indicated by an arrow 222. As illustrated in FIG. 3, which is a top view of the flow cell 200, the irradiation of the liquid sample by the laser beam 222 results in the scattering of light in various directions as indicated by arrows 326. The light rays 326 may be detected by appropriate light detectors positioned externally to the flow cell 200. The theories and mechanisms relating to light scattering and the detection of the photons represented by the resulting light rays 326 are generally understood by persons skilled in the art and thus need not be detailed herein. It will be noted, however, that in the present invention the propagations of the scattered light rays 326 to be detected are centered about the same plane as the plane along which the laser beam 222 is propagated and, like the laser beam 222, the scattered light rays 326 are thus orthogonal to the direction of liquid flow. It can be seen that the flow cell 200 is configured to enable scattered light to be detected over a wide range of angles. In one example, a plurality of external detectors (e.g., nineteen or thereabouts) may be provided to cover an angular range of detection from 20 to 150 degrees relative to the laser beam 222. It will be understood that in other examples the range of detection may be extended to values less than 20 degrees and/or greater than 150 degrees relative to the laser beam 222.

The outer surfaces of the flow cell 200 may be coated with an anti-reflection coating to minimize internal reflection of the laser beam 222 and the scattered light rays 326 back into the body of the flow cell 200. Moreover, the curvature of the sidewall 210 of the flow cell 200 assists in focusing the incoming laser beam 222 and the outgoing scattered light rays 326. The laser source may include optics to further enable a controlled focus of the laser beam 222, and the external detectors may likewise include optics to focus the scattered light rays 326 in a desired manner.

Figure 4:
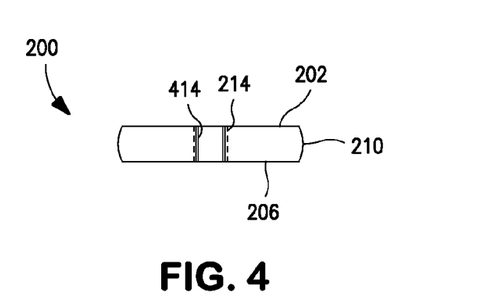
FIG. 4 is a view of an example of a flow cell similar to FIG. 2 but in which a liquid sample holder is inserted.

FIG. 4 is a view of the flow cell 200 similar to FIG. 2 but differs in that a test tube, cuvette or like liquid sample holder 414 has been inserted into the central bore 214 of the flow cell 200. Hence, as an alternative to operating as a flow-through device, the flow cell 200 may be adapted to make batch measurements of liquid samples. A refractive index matching liquid may be located annularly between the outer surface of the liquid sample holder 414 and the inner surface of the central bore 214 to reduce the effects of undesired scattering and refraction at the interface. As a further alternative, batch measurements may be made without the use of the cuvette 414 by flowing a slug of liquid sample through the central bore 214 and then stopping the flow, after which time the laser beam 222 is activated and the optical signals from the resulting scattered light rays 326 are acquired. Batch measurements are particularly useful in cases where the analytes of interest are precious and recovery (without dilution) after analysis is imperative.

Figure 5:
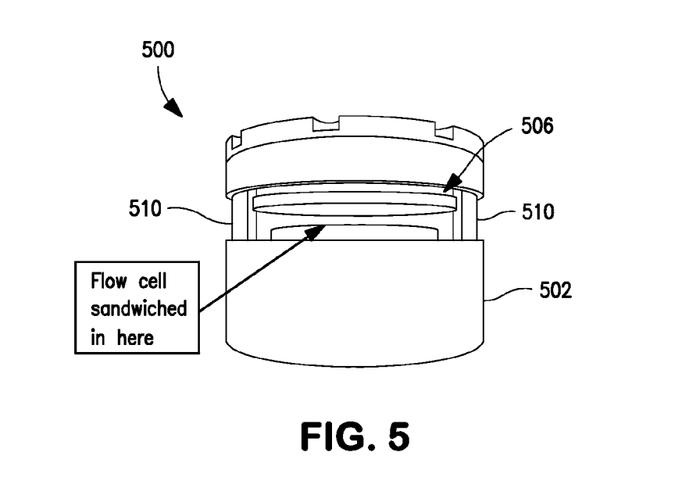
FIG. 5 is an elevation view of an example of a flow cell holder in accordance with an implementation of the present invention.

FIG. 5 is an elevation view of an example of a flow cell holder 500 that may be utilized to support the flow cell 200 in precise optical alignment with a laser beam and light detectors, for example, with the laser beam passing exactly through, and orthogonal to, the central axis of the central bore of the flow cell, and with the light detectors positioned to receive the scattered light rays along the same plane as the laser beam. Here, the term "orthogonal" encompasses "substantially orthogonal." This applies in particular to the laser beam. To reduce the effects of reflected light passing back into the laser and disturbing the monitor photodiode, it is often desirable to direct the laser at a very small angle to the normal so that back reflections propagate away from the axis of laser beam propagation.

The flow cell holder 500 generally includes a base or bottom portion 502 and a top portion 506 separated by one or more spacers 510. The flow cell (not shown) is securely installed between the top portion 506 and the bottom portion 502 in a sandwiched or stacked arrangement. The number of spacers 510 and their dimensions are minimized so as to maximize the amount of the sidewall 210 of the flow cell 200 accessible by external light detectors, thereby enabling scattered light to be detected over a wide range of angles. In the illustrated example, the two opposing spacers 510 may serve as fixtures for mounting a laser source and a laser dump (not shown). The bottom portion 502 may serve as a liquid inlet structure by providing a liquid inlet path to the central bore 214 of the flow cell 200 and the top portion 506 may serve as a liquid outlet structure by providing a liquid outlet path from the central bore 214 of the flow cell 200, or vice versa.

Figure 6A:
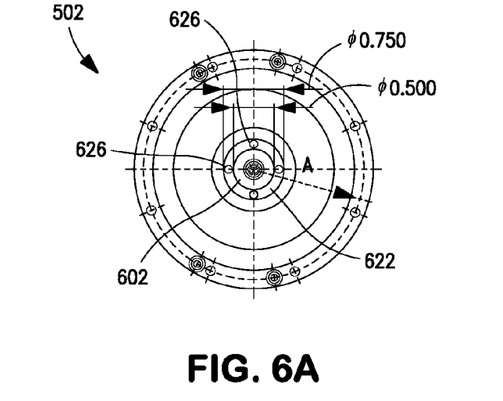
FIG. 6A is a top plan view of a bottom portion of the flow cell holder illustrated in FIG. 5.
Figure 6B:
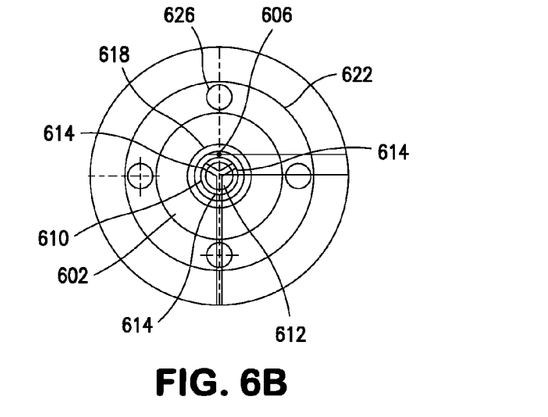
FIG. 6B is a close-up view corresponding to detail A of FIG. 6A.
Figure 6C:
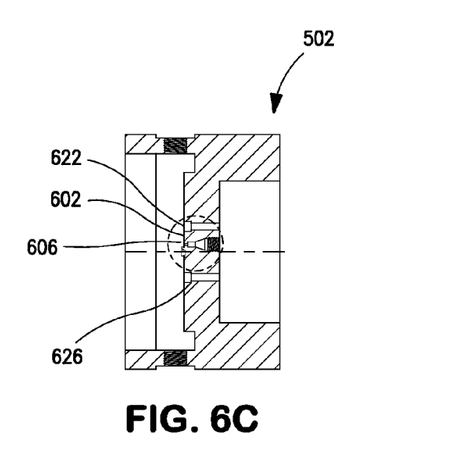
FIG. 6C is a cross-sectional side view of the bottom portion illustrated in FIG. 6A.
Figure 6D:
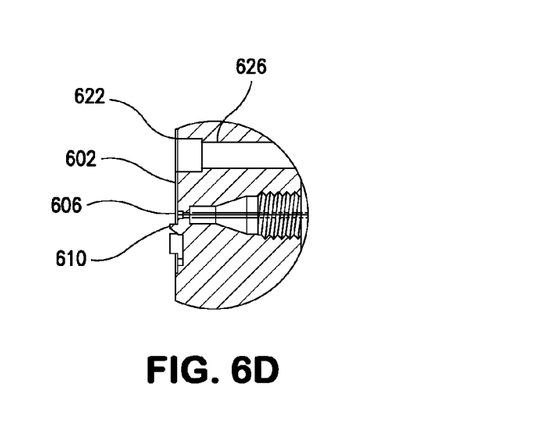
FIG. 6D is a close-up view corresponding to detail K in FIG. 6C.

FIG. 6A is a top plan view of the bottom portion 502 of the flow cell holder 500, FIG. 6B is a close-up view corresponding to detail A of FIG. 6A, FIG. 6C is a cross-sectional side view of the bottom portion 502, and FIG. 6D is a close-up view corresponding to detail K in FIG. 6C. The bottom portion 502 may have a top surface 602 that faces the bottom surface 206 of the flow cell 200. One or more liquid inlet ports 606 are formed at the top surface 602 and may be offset from the central axis of the bottom portion 502. The inlet port 606 may fluidly communicate with a liquid conduit on the opposing side of the top surface 602. Incoming liquid sample may be flowed to the liquid conduit via appropriate fittings, tubing (e.g., HPLC tubing) or the like. The inlet port 606 may be formed in or near a protruding section 610 that projects upward from the top surface 602. The protruding section 610 may have a cavity 612 facing the hollow bore 214 of the flow cell 200. The cavity 612 may have a conical, domed, or other inclined or curved shape. A plurality of radial grooves 614 may be formed in the protruding section 610. In the illustrated example, there are three radial grooves 614 angled 120 degrees from each other, effectively splitting the protruding section 610 into three sections. Each groove 614 may fluidly communicate with the inlet port 606 (or a corresponding inlet port 606 if more than one is provided). Incoming liquid sample flows from the inlet port(s) 606, through the grooves 614 and into the hollow bore 214 of the flow cell 200. The structural configuration of the liquid inlet, including the splitting of the inlet flow into three initially separate streams, produces a laminar liquid flow path into the central bore 214 of the flow cell 200. The laminar flow is optimal for optics-based measurements of the liquid sample. The inlet port 606 and the protruding section 610 may be surrounded by a circular groove 618 that positions an elastomeric seal (e.g., a PTFE gasket, not shown). When assembled, the seal is seated at the central bore 214 and seals the interface between the bottom portion 502 and the flow cell 200 to provide a liquid-tight seal. A circular channel 622 may also be formed in the bottom portion 502 and communicate with liquid drain ports 626 in case leaking occurs.

Figure 7A:
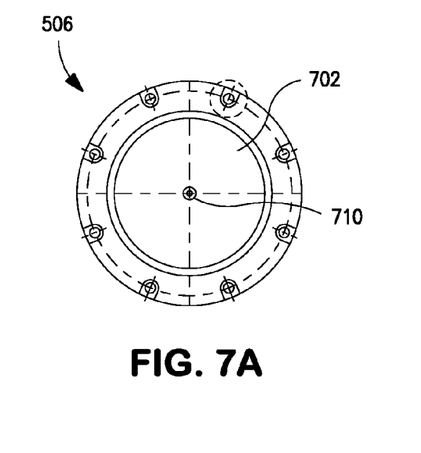
FIG. 7A is a bottom plan view of a top portion of the flow cell holder illustrated in FIG. 5.
Figure 7B:
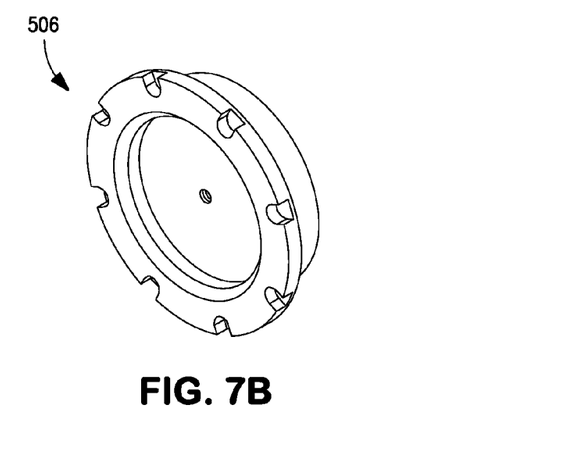
FIG. 7B is a perspective view of the top portion illustrated in FIG. 7A.
Figure 7C:
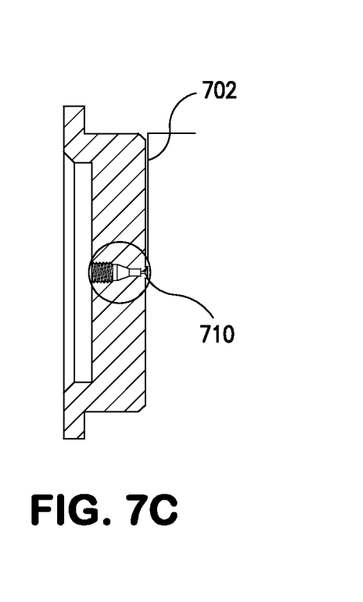
FIG. 7C is a cross-sectional side view of the top portion illustrated in FIG. 7A.
Figure 7D:
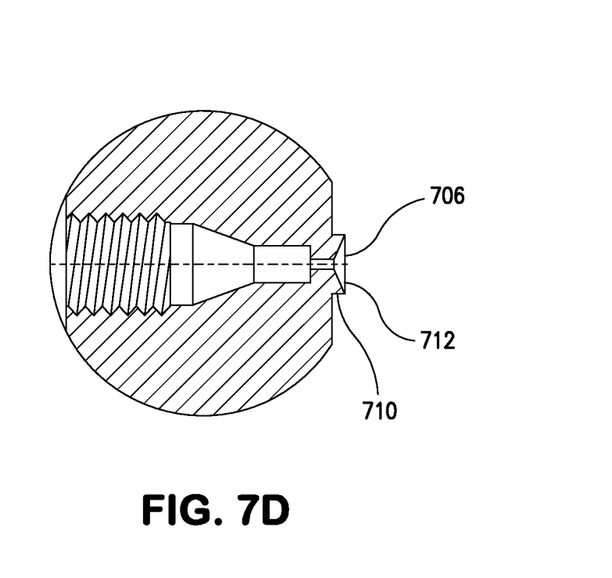
FIG. 7D is a cross-sectional close-up view corresponding to detail B of FIG. 7C.

FIG. 7A is a bottom plan view of the top portion 506 of the flow cell holder 500, FIG. 7B is a perspective view of the top portion 506, FIG. 7C is a cross-sectional side view of the top portion 506, and FIG. 7D is a cross-sectional close-up view corresponding to detail B of FIG. 7C. The top portion 506 may have a bottom surface 702 that faces the top surface 202 of the flow cell 200. A liquid outlet port 706 is formed at the bottom surface 702. The outlet port 706 may fluidly communicate with a liquid conduit on the opposing side of the bottom surface 702. Outgoing liquid sample may be flowed to the liquid conduit via appropriate fittings, tubing (e.g., HPLC tubing) or the like. The outlet port 706 may be formed in a protruding section 710 (e.g., a nipple) that projects downward from the bottom surface 702. The protruding section 710 may have a cavity 712 facing the hollow bore 214 of the flow cell 200. The cavity 712 may have a conical, domed, or other inclined or curved shape. A circular seal (not shown) may be positioned around the protruding section 710. When assembled, the seal is seated at the central bore 214 of the flow cell 200 and seals the interface between the top portion 506 and the flow cell 200 to provide a liquid-tight seal. It will be noted that the top portion 506 and/or the bottom portion 502 of the flow cell holder 500 may be adapted as needed to accommodate the use of a liquid sample holder 414 for batch operations such as described above in conjunction with FIG. 4.

Figure 8:
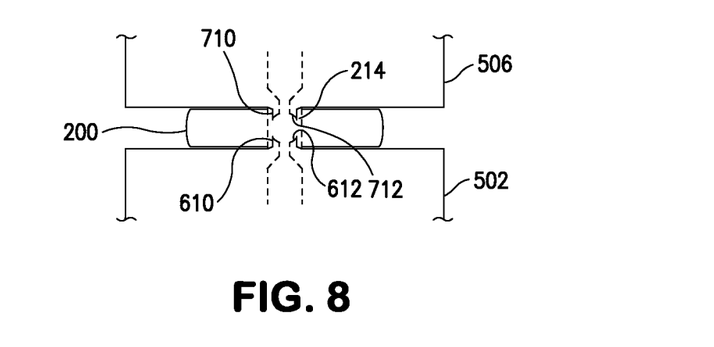
FIG. 8 is a cross-sectional elevation view of a flow cell installed between the top portion and the bottom portion of the flow cell holder illustrated in FIG. 5.

FIG. 8 is a cross-sectional elevation view of the flow cell 200 installed between the top portion 506 and the bottom portion 502 of the flow cell holder 500. The respective protruding sections 710 and 610 of the top portion 506 and the bottom portion 502 project into the central bore 214 of the flow cell 200. The protruding sections 710 and 610 serve at least three advantageous functions. First, the protruding sections 710 and 610 assist in ensuring that the central bore 214 of the flow cell 200, upon the flow cell 200 being clamped between the top portion 506 and the bottom portion 502, will be centered relative to the top portion 506 and the bottom portion 502 in a repeatable manner. Thus, the volume of liquid sample residing in the central bore 214, from one test run to another test run, will likewise be centered and in proper optical alignment with and distance from the laser source and the light detectors. Second, the protruding sections 710 and 610 reduce the volume of the central bore 214, thereby minimizing the volume of the liquid sample to be irradiated. Consequently, mixing within the volume of the central bore 214 is minimized, which in turn produces narrower peaks and higher resolution in the acquired data as appreciated by persons skilled in the art. Third, each protruding section 710 and 610 has a respective cavity 712 and 612 defined by inclined or curved walls. Thus, at the liquid inlet, the cavity 612 of the protruding section 610 enables incoming liquid to gradually decelerate, and at the liquid outlet, the cavity 712 of the protruding section 710 enables exiting liquid to gradually accelerate. This configuration reduces turbulence and consequently band broadening, which is a significant advantage for high resolution instruments.

Figure 9:
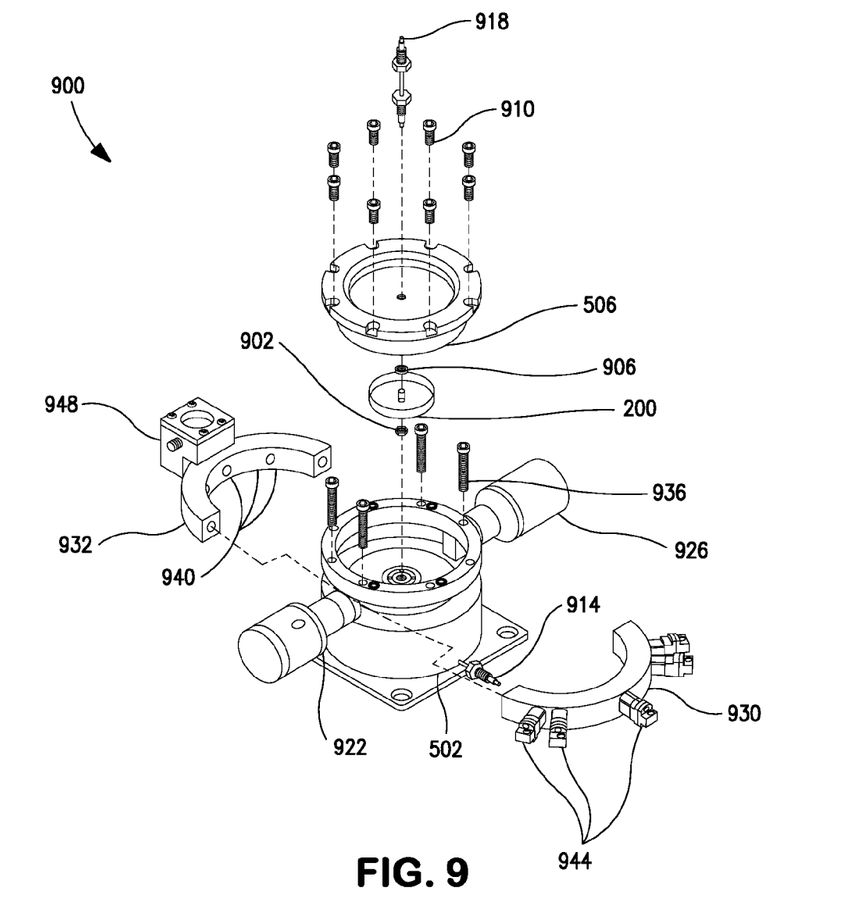
FIG. 9 is an exploded, perspective view of an example of a light scattering and detection assembly in accordance with an implementation of the present invention.

FIG. 9 is an exploded, perspective view of an example of a light scattering and detection assembly 900 that may include the flow cell 200 and flow cell holder 500. The flow cell 200 is clamped between the top portion 506 and the bottom portion 502 in a self-aligning manner as described above, with seal rings 906 and 902 providing sealed interfaces between the flow cell 200 and the respective top portion 506 and bottom portion 502. The stacked arrangement of the top portion 506, flow cell 200 and bottom portion 502 may be secured in any suitable manner, one example being the illustrated pattern of threaded members 910. Suitable liquid inlet plumbing 914 and liquid outlet plumbing 918 (fittings, conduits, etc.) may be coupled to the bottom portion 502 and the top portion 506 as needed. A laser source 922 and an opposing laser dump 926 may be mounted to the spacers 510 in proper orthogonal (or substantially orthogonal) alignment with the central axis of the central bore 214 (FIG. 2) of the flow cell 200.

One or more detector mounting members 930 and 932 may be mounted in the circumferential space radially between the laser source 922 and the laser dump 926. In the illustrated example, two semi-circular or half-ring shaped detector mounting members 930 and 932 are secured to the flow cell holder 500 by suitable fastening means such as threaded members 936. Each detector mounting member 930 and 932 has a plurality of mounting bores 940 oriented radially relative to the central axis of the flow cell 200, and at desired angles relative to the laser beam emitted by the laser source 922. The mounting bores 940 may open at a curved surface of the mounting member 930 or 932 that faces toward and is parallel with the spherical sidewall 210 (FIG. 2) of the flow cell 200. The mounting bores 940 are configured to interchangeably receive at least two types of light detectors, static detectors 944 and dynamic detectors 948. By interchangeable is meant that any one mounting bore 940 may receive either a static detector 944 or a dynamic detector 948 as desired. In the illustrated example, five static detectors 944 are mounted to one detector mounting member 930 (one static detector 944 positioned ninety degrees away from the laser axis, two static detectors 944 positioned less than ninety degrees, and two static detectors 944 positioned greater than ninety degrees) and one dynamic detector 948 is mounted to the other detector mounting member 932 ninety degrees away from the laser axis. The number of static detectors 944 and dynamic detectors 948, as well as their angular positions along the central plane of the flow cell 200, may be varied. Accordingly, a number of different detecting configurations are possible. Each detector mounting member 930 and 932 is configured so as to offer a number of different configurations. Additional configurations are made possible by replacing one or both illustrated detector mounting members 930 and 932 with other detector mounting members having more or less mounting bores 940 and mounting bores 940 located at angles different from those illustrated in FIG. 9. In all such configurations, the respective optical inlets of the as-mounted detectors 944 and/or 948 are optically aligned with radii directed from the center of the flow cell 200 and lying in the same central plane (horizontal in the present example) in which the laser beam propagates. Thus, the as-mounted detectors 944 and/or 948 are positioned to receive scattered light rays 326 (FIG. 3) propagating along corresponding radii orthogonal to the central axis of the hollow bore 214 of the flow cell 200 and, in the case of a flow-through operation, orthogonal to the velocity vector of the flowing liquid sample. By this configuration, optical detection is independent of the fluid velocity vector.

Figure 10:
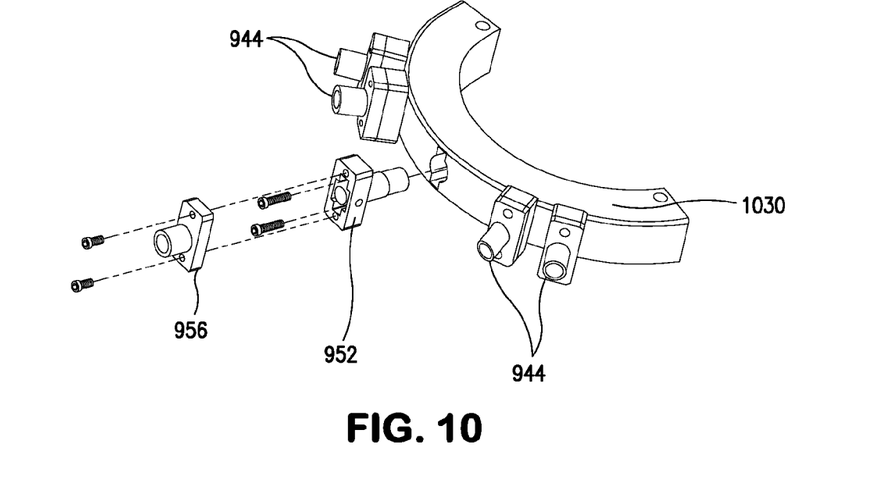
FIG. 10 illustrates an example of a detector mounting member in accordance with an implementation of the present invention, in which five static detectors are mounted.
Figure 11:
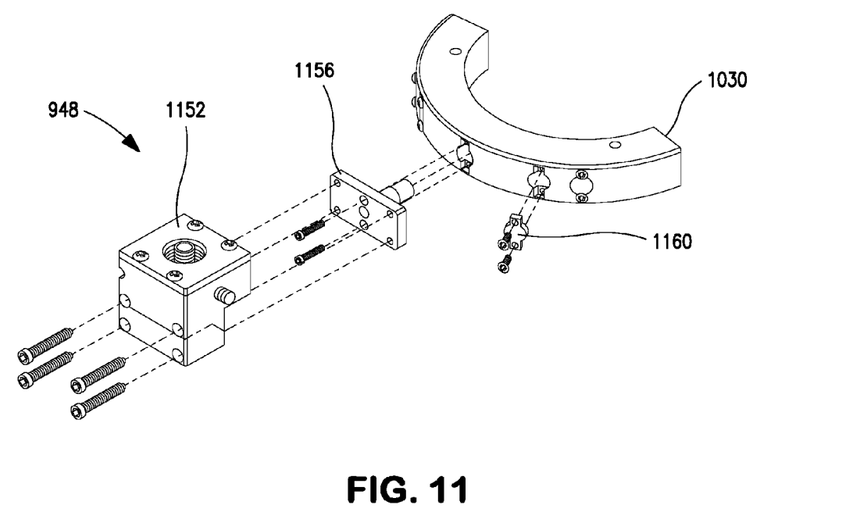
FIG. 11 illustrates the same detector mounting member as in FIG. 10, but with a single dynamic detector mounted at one of the mounting bores provided with the detector mounting member.
Figure 12:
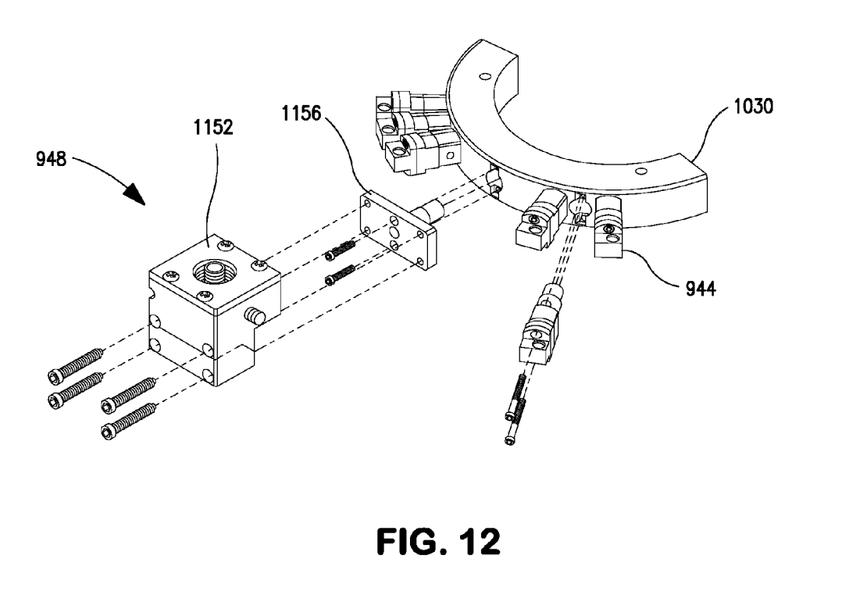
FIG. 12 illustrates another example of a detector mounting member adapted to receive at least one dynamic detector and up to six static detectors.
Figure 13:
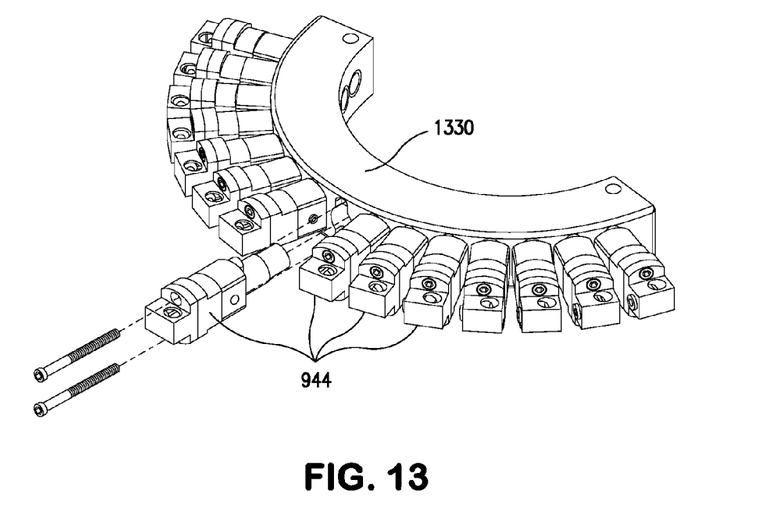
FIG. 13 illustrates another example of a detector mounting member adapted to receive up to fifteen static detectors.

Accordingly, additional examples of detector mounting members are illustrated in FIGS. 10-13. FIG. 10 illustrates a detector mounting member 1030 in which five static detectors 944 are mounted. Each static detector 944 may include a housing 952 containing optics and the detector element (e.g., a photodiode), and a cover plate 956 that includes a desired fitting such as an SMA connector. FIG. 11 illustrates the same detector mounting member 1030 as in FIG. 10, but with a single dynamic detector 948 mounted at one of the mounting bores 940. The dynamic detector 948 may include a housing 1152 containing optics and the detector element (e.g., a photodiode), and another housing 1156 containing a collimator lens. In the example of FIG. 11, the other radial mounting bores 940 are not being utilized and thus may be covered with detachable covers 1160. FIG. 12 illustrates another detector mounting member 1230 adapted to receive at least one dynamic detector 948 and up to six static detectors 944. FIG. 13 illustrates another detector mounting member 1330 adapted to receive up to fifteen static detectors 944.

Figure 14:
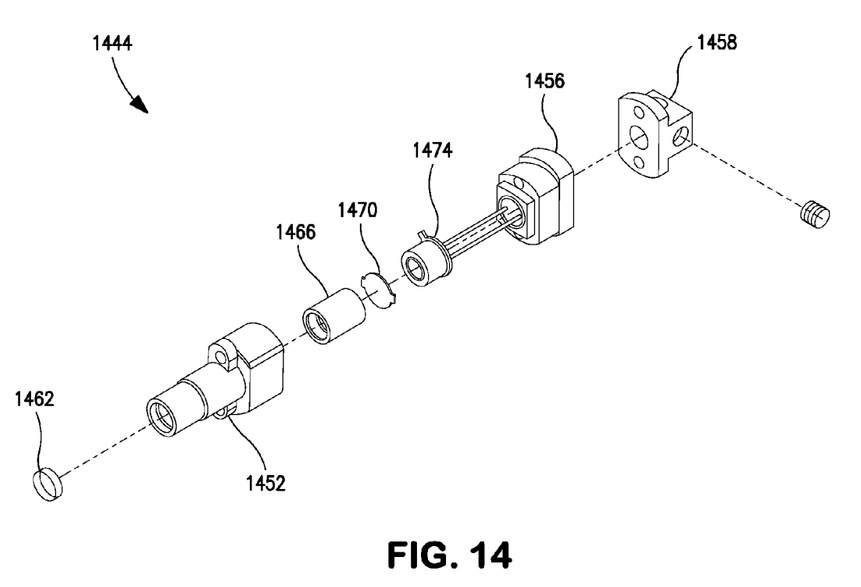
FIG. 14 is an exploded, perspective view of another example of a static detector.

FIG. 14 is an exploded, perspective view of another example of a static detector 1444. The static detector 1444 includes two or more housing portions 1452, 1456 and 1458. A collimator lens 1462 is positioned so as to face the curved sidewall of the flow cell and receive a scattered light ray therefrom. A focusing lens 1466 is positioned at a distance from the collimator lens 1462 along the optical axis, and may be followed by an aperture 1470 that may be adjustable as needed for focusing the static detector 1444 on the center of the flow cell. A photodiode 1474 serves as the detecting element that collects the optical signals propagating from the flow cell along the optical axis of this static detector 1444.

Figure 15:
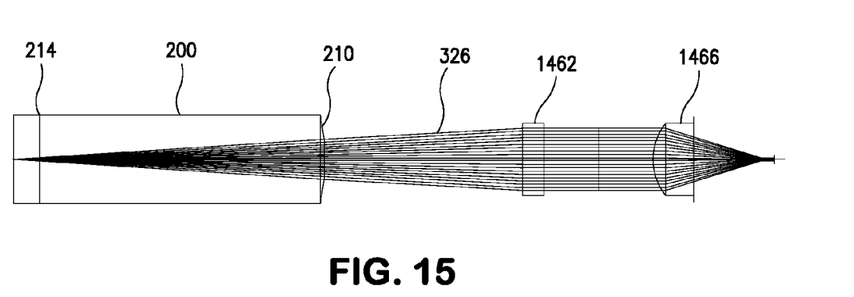
FIG. 15 schematically illustrates the collection optics involved in acquiring data from a scattered light ray in accordance with an implementation of the present invention.

FIG. 15 schematically illustrates the collection optics involved in acquiring data from a scattered light ray 326. Included in FIG. 15 are one half of the flow cell 200 and the collimator lens 1462 and focusing lens 1466 of the static detector. As the light ray 326 propagates radially outward from the central bore 214 of the flow cell 200, it disperses somewhat in a conical solid angle. Because the sidewall 210 (i.e., the solid-air interface) of the flow cell 200 is spherical, the light ray 326 will emanate in a direction normal to this curved surface 210, i.e., the light ray 326 will not bend or otherwise be adversely affected by the sidewall 210. The light ray 326 is then collimated by the collimator lens 1462, and subsequently focused by the focusing lens 1466 onto the photodiode or other detecting element of the detector. It again can be seen that the optical signal 326 produced by the scattering effect of the flow cell 200 propagates along the same plane as the laser beam, and like the laser beam is orthogonal to the axis of the central bore. Moreover, the light ray 326 even as it spreads out in a solid angle remains centered about the same plane along which all detector optics are aligned, thereby ensuring a strong detection signal. In the case of a flow-through operation, the laser beam is orthogonal to the direction of the velocity of the liquid sample flow. By this configuration, the acquisition of optical data is independent of the flow velocity, which minimizes artifacts in the data particularly in the case of dynamic detectors. In addition, the polarization of the laser beam is perpendicular to the plane of detection, thereby ensuring a strong detection signal.

Figure 16:
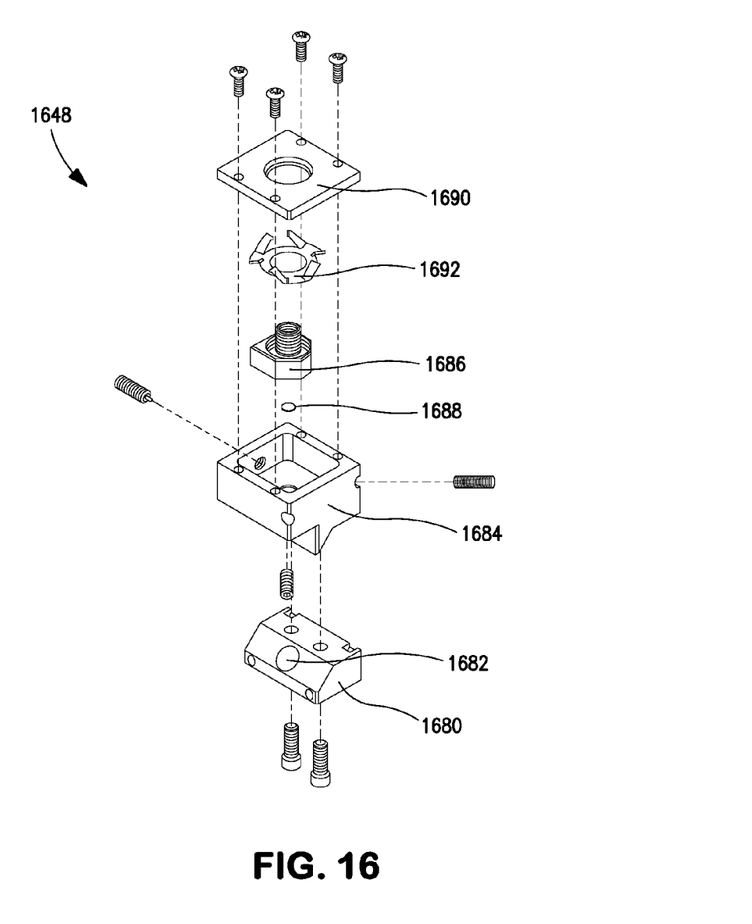
FIG. 16 is an exploded, perspective view of an example of a dynamic detector.

FIG. 16 is an exploded, perspective view of an example of a dynamic detector 1648. The dynamic detector 1648 includes a lower mirror assembly 1680 that receives incoming scattered light rays via the mounting bore of the detector mounting member. The lower mirror assembly 1680 includes a mirror 1682. An upper mirror assembly 1684 is coupled to the lower mirror assembly 1680. An optical fiber carrier assembly 1686 is mounted in the upper mirror assembly 1684 in alignment with a slit 1688. A top cover 1690 is clamped to the upper mirror assembly 1684 and has a bore through which the connector of the optical fiber carrier assembly 1686 may protrude. The mounting and positioning of the optical fiber carrier assembly 1686 may be biased by a disc spring 1692.

Figure 17:
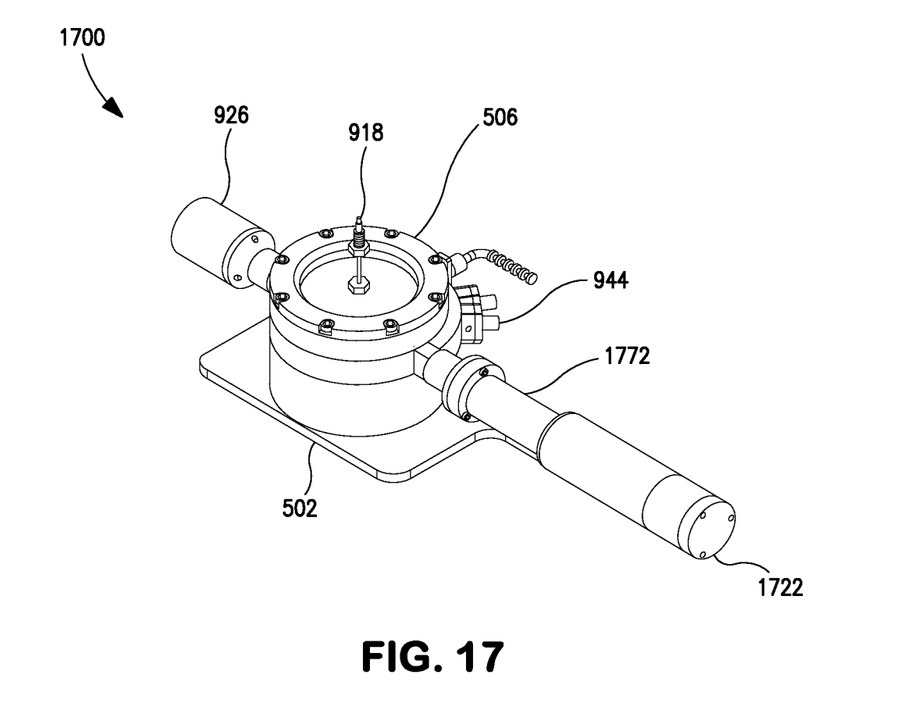
FIG. 17 is a perspective view of another example of a light scattering and detection assembly in accordance with an implementation of the present invention.

FIG. 17 is a perspective view of another example of a light scattering and detection assembly 1700, which includes a laser assembly 1722 adapted for high-temperature operations. The laser assembly 1722 includes an extension tube 1772 that in practice extends through the insulated wall of an oven. The extension tube 1772 may be constructed from a material having a low coefficient of thermal expansion such as, for example, Invar alloy, which is an iron-nickel alloy containing 40-50% nickel. The laser assembly 1722 may be supported by one or more brackets. Accordingly, the flow c-ell 200 (FIG. 9) in this example is positioned within the oven while delicate components of the laser assembly 1722 are located outside of the oven. Sensitive components of the detectors 944 may also be located outside of the oven and may receive the optical signals from the flow cell 200 via optical fibers. This configuration is useful for studying molecules that require an elevated temperature such as, for example, 140° C. For instance, many polymers such as polyethylene and polypropylene are soluble only at elevated temperatures and thus it is necessary to heat the polymers to separate them by column chromatography. Also, the viscosity of some solvents is too high to permit chromatographic techniques to be utilized unless the viscosity is reduced by elevating the temperature of the solvent. Additional details regarding the high-temperature laser assembly 1722, as employed in another light-scattering context, are disclosed in U.S. Pat. No. 5,701,176, the content of which is incorporated herein in its entirety.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A flow cell device, comprising:
a solid flow cell body constructed entirely of an optically transmitting material and comprising an outer surface and a hollow bore oriented along a central axis, the outer surface comprising:
a circular liquid inlet surface orthogonal to the central axis;
a circular liquid outlet surface orthogonal to the central axis and parallel to the liquid inlet surface; and
a sidewall extending between the liquid inlet surface and the liquid outlet surface and coaxially surrounding the hollow bore,
wherein the hollow bore comprises a liquid inlet end on the central axis at the liquid inlet surface and a liquid outlet end on the central axis at the liquid outlet surface;
a liquid inlet structure facing the liquid inlet surface and comprising a first protruding section contacting the liquid inlet end and extending through the liquid inlet end into the hollow bore, the liquid inlet structure having a liquid inlet port formed in the first protruding section and fluidly communicating with the hollow bore; and
a liquid outlet structure facing the liquid outlet surface and comprising a second protruding section contacting the liquid outlet end and extending through the liquid outlet end into the hollow bore, the liquid outlet structure having a liquid outlet port formed in the second protruding section and fluidly communicating with the hollow bore.

2. The flow cell device of claim 1, wherein the liquid inlet structure has a plurality of radial grooves formed in the first protruding section, the plurality of radial grooves extending radially relative to the central axis and fluidly communicating with the hollow bore, and the liquid inlet port is positioned in fluid communication with the radial grooves.

3. The flow cell device of claim 1, wherein the first protruding section has a first cavity facing the hollow bore such that a cross-sectional area of the first cavity increases in the direction of the hollow bore, and the second protruding section has a second cavity facing the hollow bore such that a cross-sectional area of the second cavity decreases in the direction away from the hollow bore.

4. The flow cell device of claim 1, wherein the sidewall has a spherical outer profile.

5. The flow cell device of claim 1, further comprising a laser source oriented relative to the flow cell body so as to direct a laser beam along a central plane of the flow cell body and through the hollow bore, the central plane being orthogonal to the central axis.

6. The flow cell device of claim 5, wherein the hollow bore establishes a liquid flow path along the central axis from the liquid inlet port to the liquid outlet port, and the laser source is configured to direct the laser beam orthogonally relative to the liquid flow path.

7. The flow cell device of claim 1, further comprising one or more light detectors oriented relative to the flow cell body so as to receive one or more light rays propagating from the hollow bore and along a central plane of the flow cell body and through the hollow bore, the central plane being orthogonal to the central axis.

8. The flow cell device of claim 7, wherein the hollow bore establishes a liquid flow path along the central axis from the liquid inlet port to the liquid outlet port, and the one or more light rays received by the one or more light detectors propagate orthogonally relative to the liquid flow path.

9. The flow cell device of claim 7, wherein the one or more light detectors are oriented at angles ranging from 20 to 150 degrees relative to the laser beam.

10. The flow cell device of claim 1, further comprising a liquid sample holder removably inserted in the hollow bore.

11. The flow cell device of claim 1, wherein the flow cell body comprises a central plane orthogonal to the central axis, and at least a portion of the outer surface is spherical, and further comprising a mounting member, the mounting member comprising a curved surface facing the flow cell body and parallel with the spherical outer surface portion, and a plurality of radial mounting bores opening at the curved surface, the radial mounting bores having respective mounting bore axes collinear with respective radii extending from the hollow bore along the central plane at different angles relative to the central axis.

12. The flow cell device of claim 11, further comprising one or more light detectors mounted at one or more of the radial mounting bores, each light detector including an optical inlet aligned with a corresponding radius extending along the central plane.

13. The flow cell device of claim 12, further comprising a laser source oriented relative to the flow cell body so as to direct a laser beam along the central plane and through the hollow bore.

14. The flow cell device of claim 12, wherein the one or more light detectors include a static light detector and a dynamic light detector.

15. The flow cell device of claim 1, wherein the liquid inlet structure is secured to the liquid outlet structure by a fastener and the flow cell body is clamped between the liquid inlet structure and the liquid outlet structure.

16. A method for making a light-scattering measurement of a liquid sample, the method comprising:
  introducing the liquid sample into the hollow bore of the flow cell device of claim 1;
  directing an electromagnetic beam through the flow cell body and into the hollow bore along a central plane of the flow cell body orthogonal to the central axis, to irradiate the liquid sample and produce a light ray;
  directing the light ray along the central plane away from the hollow bore; and
  receiving the light ray at a light detector positioned along the central plane and external to the flow cell body.

17. The method of claim 16, wherein introducing the liquid sample comprises flowing the liquid sample along a liquid flow path from the liquid inlet port, through the hollow bore and to the liquid outlet port, and wherein the electromagnetic beam and the light ray propagate orthogonal to the liquid flow path.

18. The method of claim 16, wherein the sidewall is spherical, and directing the light ray includes passing the liquid ray through the spherical sidewall.

19. A method for assembling the flow cell device of claim 1, comprising assembling the flow cell body between the liquid inlet structure and the liquid outlet structure, by contacting the first protruding section with the liquid inlet end and contacting the second protruding section with the liquid outlet end.

20. The method of claim 19, further comprising mounting a plurality of light detectors to a plurality of radial mounting bores of a mounting member, the mounting member comprising a curved surface facing the flow cell body and parallel with a spherical outer surface portion of the flow cell body, wherein the radial mounting bores open at the curved surface and have respective mounting bore axes collinear with respective radii extending from the hollow bore along a central plane at different angles relative to a central axis orthogonal to the central plane.

* * * * *